United States Patent
Nagai

(10) Patent No.: US 10,126,229 B2
(45) Date of Patent: Nov. 13, 2018

(54) OPTICAL MEASUREMENT DEVICE

(71) Applicant: Shimadzu Corporation, Kyoto-shi, Kyoto (JP)

(72) Inventor: Yusuke Nagai, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 0 days.

(21) Appl. No.: 15/567,695

(22) PCT Filed: Apr. 24, 2015

(86) PCT No.: PCT/JP2015/062541
§ 371 (c)(1),
(2) Date: Oct. 19, 2017

(87) PCT Pub. No.: WO2016/170681
PCT Pub. Date: Oct. 27, 2016

(65) Prior Publication Data
US 2018/0088027 A1 Mar. 29, 2018

(51) Int. Cl.
*G01N 21/05* (2006.01)
*G01N 21/03* (2006.01)
(Continued)

(52) U.S. Cl.
CPC ........... *G01N 21/05* (2013.01); *G01N 21/031* (2013.01); *G01N 2021/052* (2013.01); *G01N 2021/6482* (2013.01); *G01N 2021/651* (2013.01)

(58) Field of Classification Search
CPC ............... G01N 21/8507; G01N 21/31; G01N 21/0303; G01N 21/59; G01N 21/05
(Continued)

(56) References Cited

U.S. PATENT DOCUMENTS 3,879,615 A * 4/1975 Moser ............... G01N 15/0205
250/574
5,680,209 A 10/1997 Mächler
6,108,083 A * 8/2000 Machler .................. G01J 3/02
356/246

FOREIGN PATENT DOCUMENTS

EP 0655128 A1 5/1995
JP 5-172732 A 7/1993
(Continued)

OTHER PUBLICATIONS

International Preliminary Report on Patentability (Form PCT/IB/373) issued in counterpart International Application No. PCT/JP2015/062541 dated Oct. 24, 2017, with Written Opinion (Form PCT/ISA/237) (9 pages).
(Continued)

*Primary Examiner* — Md M Rahman
(74) *Attorney, Agent, or Firm* — Westerman, Hattori, Daniels & Adrian, LLP

(57) ABSTRACT

Measurement light is cast from a light-casting unit into a flow cell. The light is repeatedly reflected at an outer surface of the flow cell. A detecting unit including a connecting element and a photodetector element is provided in contact with the outer surface of the flow cell. Since the connecting element is made of a material whose refractive index is higher than that of the wall of the flow cell, the light is extracted from the flow cell at the contact position of the connecting element, to be detected by the photodetector element. A shift of the attachment position of the detecting unit along the axis of the flow cell changes the optical path length of the measurement light. A high-sensitivity absorption measurement can be performed by controlling the optical path length by merely changing the attachment position of the detecting unit, without replacing the flow cell.

7 Claims, 3 Drawing Sheets

(51) Int. Cl.
*G01N 21/64* (2006.01)
*G01N 21/65* (2006.01)

(58) Field of Classification Search
USPC .......................................................... 356/436
See application file for complete search history.

(56) References Cited

FOREIGN PATENT DOCUMENTS

| | | |
|---|---|---|
| JP | 8-500183 A | 1/1996 |
| JP | 2001-343327 A | 12/2001 |
| JP | 2011-237384 A | 11/2011 |
| WO | 94/04892 A1 | 3/1994 |

OTHER PUBLICATIONS

"Kou Kussetsuritsu No LED You Tei Koudo Erasutomah Geru Fuushizai 3 Seihin 3 Gatsu Joujun Hatsubai (Three Products of High Refractive Index Low Hardness Elastomer and Gel Seal Materials for LED to be Available Early in March)", [online], Dow Coming Toray Co., Ltd., [accessed on Apr. 16, 2015], the Internet <URL: http://www.dowcoming.co.jp/ja_JP/content/japan/japan company/ nr080304.aspx>, (2 pages).
International Search Report dated Jul. 21, 2015, issued in counterpart International Application No. PCT/JP2015/062541 (1 page).

* cited by examiner

Fig. 9A SAMPLE LIQUID
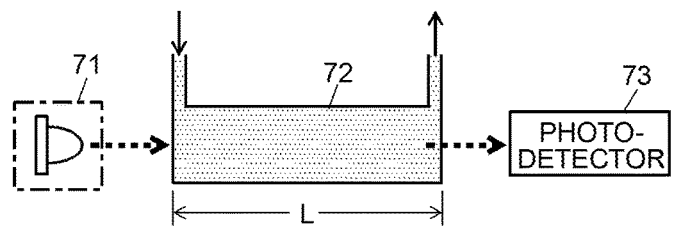
Fig. 9B SAMPLE LIQUID
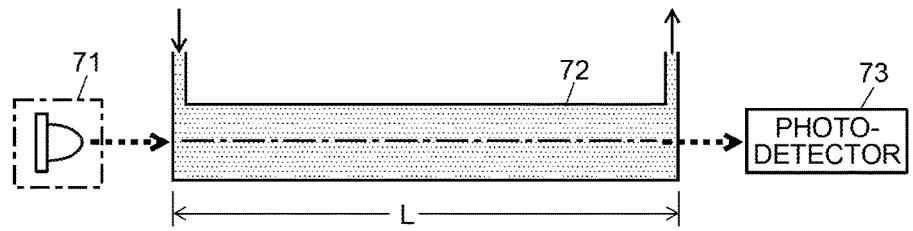

OPTICAL MEASUREMENT DEVICE

TECHNICAL FIELD

The present invention relates to an optical measurement device for casting light into a sample liquid in a cell and for detecting an emission of light obtained from the sample liquid in response to the cast light, such as transmitted light, scattered light or fluorescence.

BACKGROUND ART

As a detector for a liquid chromatograph (LC), an optical measurement device for measuring the absorbance (or transmittance) of a sample liquid exiting from a column is frequently used. FIGS. 9A and 9B are schematic configuration diagrams of one example of the optical measurement device for absorption measurement (for example, see Patent Literature 1).

Measurement light emitted from the LED 71 serving as the light source is cast into a flow cell 72 through which a sample liquid is passed. While passing through the sample liquid in the flow cell 72, the measurement light undergoes absorption in a manner that depends on the kind and amount of a component in the sample liquid. The light which has undergone such an absorption enters a photodetector 73. The photodetector 73 produces a detection signal corresponding to the amount of that light. In a signal processing unit (not shown), the absorbance by the sample liquid is calculated from the detection signal. In the present configuration, the length L of the flow cell becomes the optical path length in the sample liquid.

There are several types of flow cells used in such an optical measurement device. For example, in a preparative separation LC in which a sample liquid containing components separated from each other with a column is divided into fractions using a fraction collector, since the concentration of the sample liquid is usually higher than in normal analyses, the absorbance per unit length of the optical path is high. Therefore, a flow cell having a relatively short optical path length is used, as shown in FIG. 9A, in order to enhance the detection sensitivity. By comparison, in the case of analyzing a trace amount of sample, i.e. a low-concentration sample, a flow cell having a relatively long optical path length is used, as shown in FIG. 9B, in order to enhance the detection sensitivity. In this manner, in an optical measurement device for LC, flow cells having different optical path lengths are selectively used according to the purpose of the analysis or other factors.

As just mentioned, the conventional and common method of changing the optical path length in a sample liquid in an optical measurement device is to entirely replace the used flow cell with another one. However, replacing the flow cell requires a considerable amount of time and labor. Furthermore, in order to allow the optical path length to be finely changed in multiple stages, a plurality of flow cells with different lengths need to be prepared.

To address this problem, an optical measurement device has been proposed in which the angle of incidence of the measurement light from the light source onto the flow cell can be changed so as to control the number of reflections of the light within the flow cell and thereby change the effective optical path length (for example, see Patent Literature 2). However, the mechanism for adjusting the incident angle of the measurement light is large in size and makes the optical measurement device accordingly large. Additionally, in order to accurately change the incident angle of the measurement light by changing the location and orientation of the light source or incident optical system, high-precision mechanical parts are needed, which increases the device cost.

CITATION LIST

Patent Literature

Patent Literature 1: JP 2011-237384 A
Patent Literature 2: JP 2001-343327 A

Non Patent Literature

Non Patent Literature 1: "Kou Kussetsuritsu No LED You Tei Koudo Erasutomah Geru Fuushizai 3 Seihin 3 Gatsu Joujun Hatsubai (Three Products of High Refractive Index Low Hardness Elastomer and Gel Seal Materials for LED to Be Available Early in March)", [online], Dow Corning Toray Co., Ltd., [accessed on Apr. 16, 2015], the Internet

SUMMARY OF INVENTION

Technical Problem

The present invention has been developed in view of the previously described problem. Its objective is to provide an optical measurement device capable of performing appropriate measurements for a wide range of concentrations of samples from low-concentration to high-concentration samples by changing the optical path length within the cell containing a sample liquid, without replacing the cell as well as without changing the angle of incidence of the measurement light on the cell.

Solution to Problem

The optical measurement device according to the present invention developed for solving the previously described problem includes:

a) an optically transparent sample cell which is a tubular container through which a sample liquid is to be passed or in which a sample liquid is to be contained;

b) a measurement-light casting unit for casting measurement light into the sample cell along the axis of the sample cell or in a direction oblique to the axis of the sample cell; and c) a detecting unit for detecting light coming from the sample cell when the measurement light is cast from the measurement-light casting unit into the sample cell, the light being either the measurement light transmitted through the sample cell or light emitted from the sample liquid in response to the measurement light, and the detecting unit including: a photodetector element for performing photoelectric conversion; and a connecting element placed between the sample cell and the photodetector element in such a manner as to have a portion being in contact with the outer surface of the sample cell, the connecting element being made of a material which allows transmission of light and whose refractive index is higher than the refractive index of the material of the wall of the sample cell, where the contact position of the detecting unit on the sample cell is changeable.

In the optical measurement device according to the present invention, for example, the sample cell is optically transparent in its entirety and is made of a material whose refractive index is higher than those of organic solvents commonly used as the solvent for sample liquids as well as that of the environment surrounding the sample cell (e.g. air). For example, synthetic silica, sapphire (single crystal of aluminum oxide: $Al_2O_3$) or diamond may be used as such a material.

The measurement-light casting unit casts measurement light into the sample cell so that the light is directed either parallel to the axis of the sample cell or obliquely to this axis at an angle of θ which satisfies 0<θ<90°. The measurement light incident on the sample cell passes through the sample liquid which fills the same cell, and is propagated through the sample cell while being repeatedly undergoing reflections (preferably, total reflections) at the outer wall surface of the sample cell (i.e. at the interface between the wall of the sample cell and the surrounding environment). That is to say, the sample cell filled with the sample liquid functions as a kind of optical waveguide. As is generally known, if a dust particle or similar contaminant is adhered to the outer surface of an optical waveguide, the light propagation efficiency deteriorates due to a leakage of light through that area. Normally, in order to avoid this problem, some measures are taken to prevent adhesion of dust particles or similar contaminants to the outer surface of the waveguide.

By comparison, the optical measurement device according to the present invention positively utilizes this leakage of light to extract and detect light from any position on the sample cell as follows: When the connecting element of the detecting unit is in contact with the outer surface of the sample cell, the light reaching the contact area is not reflected by the outer wall surface of the sample cell but penetrates into the connecting element, since the refractive index of the connecting element is higher than that of the wall of the sample cell. The light penetrates through the connecting element to the photodetector element. The photodetector element produces a detection signal corresponding to the amount of light which has reached the same element.

For example, increasing the distance of the attachment position of the detecting unit on the sample cell from the measurement-light casting unit makes the total reflection of the measurement light occur a larger number of times at the outer wall surface of the sample cell, which means that the photodetector element receives measurement light which travels longer optical path lengths on average, or fluorescence or scattered light emitted from the sample liquid in response to the measurement light which has travelled such longer optical path lengths on average. In other words, the average optical path length in the sample liquid can be changed by shifting the attachment position of the detecting unit on the sample cell along the axial direction of the sample cell.

For example, in the case of an absorbance measurement, when the sample liquid has a high concentration, the absorbance per unit length of the optical path is high. Therefore, the attachment position of the detecting unit on the sample cell is set closer to the measurement-light casting unit so as to shorten the average optical path length so that the detection signal will be prevented from being too low. Contrarily, when the sample liquid has a low concentration, the absorbance per unit length of the optical path is low. Therefore, the attachment position of the detecting unit on the sample cell is set farther from the measurement-light casting unit so as to elongate the average optical path length so that the amount of decrease in the detection signal due to the absorption will be increased and a higher level of sensitivity will be achieved.

In the case of a fluorescence measurement or Raman-scattered light measurement, when the sample liquid has a high concentration (when the number of molecules is large), the amount of fluorescent emission or scattering per unit length of the optical path is high. Therefore, the attachment position of the detecting unit on the sample cell is set closer to the measurement-light casting unit so as to shorten the average optical path length so that the detection signal will be prevented from being too high. Contrarily, when the sample liquid has a low concentration (when the number of molecules is small), the amount of fluorescent emission or scattering per unit length of the optical path is low. Therefore, the attachment position of the detecting unit on the sample cell is set farther from the measurement-light casting unit so as to elongate the average optical path length so that the detection signal will be increased and a higher level of sensitivity will be achieved.

In the optical measurement device according to the present invention, the detecting unit may be provided only at a portion of the circumference of the outer surface of the sample cell, or it may be provided over the entire circumference.

For example, if the sample cell has a cylindrical shape, the detecting unit may be shaped like an annular body having a hollow portion through which the sample cell is to be inserted.

This configuration enables the detecting unit to efficiently capture rays of light which travel through the sample cell while being totally reflected in various directions when measurement light in the form of a gradually spreading beam with a certain angle is cast from the measurement-light casting unit into the sample cell, or the fluorescence or scattered light emitted from the sample liquid in various directions due to those rays of light.

In the optical measurement device according to the present invention, the connecting element may preferably have the refractive index increasing from the surface which is in contact with the sample cell toward the surface which is in contact with the photodetector element. This reduces the difference in refractive index between the two sides facing each other across the interface between the sample cell and the connecting element as well as those facing each other across the interface between the connecting element and the photodetector element, whereby the light-passing efficiency will be improved.

The measurement light cast from the measurement-light casting unit may be either monochromatic light having a predetermined wavelength or light having a wide wavelength range. In the case of using the latter, a light-dispersing element may preferably be provided between the connecting element and the photodetector element in the detecting unit, and the wavelength-dispersed light produced by the light-dispersing element may be detected at each wavelength with the photodetector element, or a specific wavelength of light extracted by the light-dispersing element may be detected with the photodetector element.

Advantageous Effects of the Invention

In the optical measurement device according to the present invention, the optical path length in a sample liquid can be changed according to the concentration of the sample liquid, purpose of the analysis or other factors by merely changing the attachment position of the detecting unit on the sample cell. The task of changing the attachment position of the detecting unit can be easily performed by a measurer. Since it is unnecessary to perform the replacement of the flow cell or other cumbersome conventional tasks, the amount of time and labor of the measurer is reduced and the efficiency of the measurement is improved. It is unnecessary to prepare sample cells having various optical path lengths. Changing the attachment position of the detecting unit on the sample cell does not require such a large-sized mechanism as needed for adjusting the incident angle of the measurement light. This is suitable for miniaturizing the device. Furthermore, the change in the attachment position of the detecting unit causes no change in the optical path through which the measurement light is incident on the sample cell, as well as no change in the optical path within the sample cell. Therefore, no cumbersome readjustment of the optical system is needed.

BRIEF DESCRIPTION OF DRAWINGS

FIGS. 1A and 1B are sectional views at a plane containing the central axis of a flow cell, and FIG. 1C is a sectional view at a plane orthogonal to the central axis.

FIG. 6 is a schematic configuration diagram of an absorbance measurement device as another embodiment of the present invention.

FIG. 7 is a schematic configuration diagram of an absorbance measurement device as another embodiment of the present invention.

FIG. 8 is a schematic configuration diagram of an absorbance measurement device as another embodiment of the present invention.

FIGS. 9A and 9B are schematic configuration diagrams of a conventional absorbance measurement device.

DESCRIPTION OF EMBODIMENTS

Embodiments of the optical measurement device according to the present invention are hereinafter described with reference to the attached drawings.

Figure 1A:
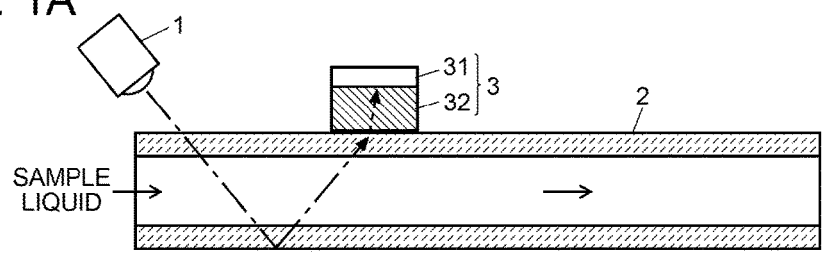
FIGS. 1A-1C are schematic configuration diagrams of an absorbance measurement device as one embodiment of the optical measurement device according to the present invention, where
Figure 1B:
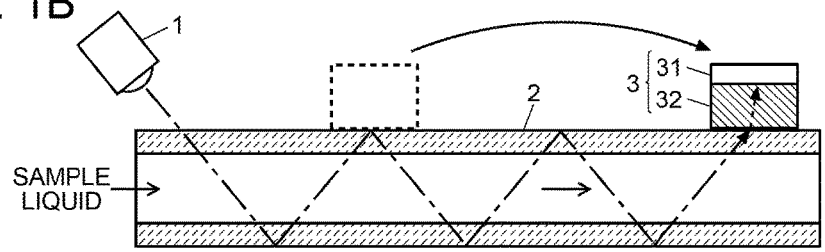
Figure 1C:
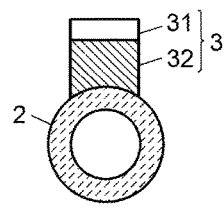
Figure 2:
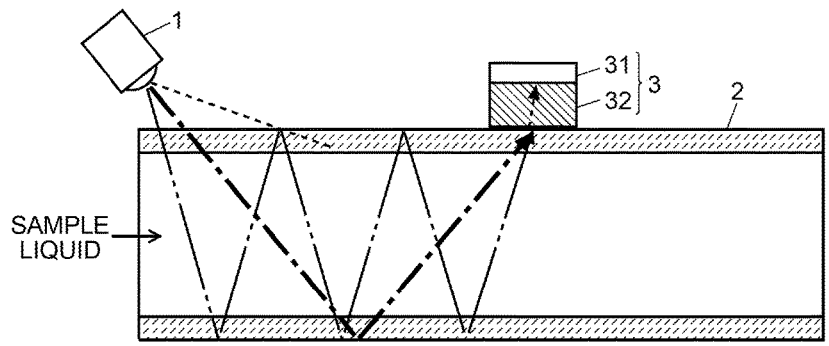
FIG. 2 is a diagram illustrating an optical path within the flow cell in the absorbance measurement device shown in FIG. 1.

FIGS. 1A-1C are schematic configuration diagrams of an absorbance measurement device according to the first embodiment, where FIGS. 1A and 1B are sectional views at a plane containing the central axis of a flow cell, and FIG. 1C is a sectional view at a plane orthogonal to the central axis. FIG. 2 is a diagram illustrating an optical path within the flow cell in the absorbance measurement device according to the present embodiment.

The absorbance measurement device in the present embodiment includes a flow cell 2 having a passage shaped like a cylindrical straight tube, a light-casting unit 1 for casting measurement light into the flow cell, and a detecting unit 3 provided in contact with the outer surface of the flow cell 2. It is hereinafter assumed that the flow cell 2 is placed in the air.

For example, the light-casting unit 1 includes a single LED as the light source. The unit is driven by a drive current supplied from an LED driver (not shown) and emits light with a narrow wavelength range that can be regarded as monochromatic light. The light emitted from the light-casting unit 1 gradually spreads with a predetermined solid angle. The positional relationship between the light-casting unit 1 and the flow cell 2 is determined so that the beam axis of the light makes a predetermined angle θ with the central axis of the flow cell 2 within a range of 0<θ<90°.

The flow cell 2 is made of a transparent material having a refractive index $n_2$ which is higher than both the refractive index $n_1$ of air (surrounding environment) and the refractive index $n_3$ of the solvent in the sample liquid flowing through the passage. If the present device is a detector for LC, various organic solvents commonly used as the mobile phase in LC can be assumed as the solvent in the sample liquid. Preferable materials for the flow cell 2 include sapphire, synthetic silica and diamond.

The detecting unit 3 includes a photodetector element 31, which is typically a semiconductor photo-detecting element (e.g. photodiode), and a connecting element 32 which has one surface being in contact with the outer surface of the flow cell 2 and the opposite surface being in contact with the light-receiving surface of the photodetector element 31. This unit can be attached at any position on the outer surface of the flow cell 2.

The connecting element 32 is made of an optically transparent or semitransparent material whose refractive index $n_4$ is equal to or higher than the refractive index $n_2$ of the material of the flow cell 2 as well as equal to or lower than the refractive index $n_5$ of the light-receiving surface of the photodetector element 31 (where $n_2 \leq n_5$). Accordingly, $n_2 < n_4 < n_5$, $n_2 < n_4 = n_5$, $n_2 = n_4 < n_5$, or $n_2 = n_4 = n_5$. The connecting element 32 should preferably be capable of coming in a particularly high degree of contact with the outer surface of the flow cell 2. Examples of the preferable materials include: refractive index dispersion polymers used for resin optical fibers or other devices; gel-like members, such as a high refractive index low hardness elastomer and gel-like seal material for LED (see Non Patent Literature 1 or other documents); and silicone. Matching oil used in an optical measurement using a prism or similar processes is also usable. Gelatin may also be used.

A measurement operation in the case where the detecting unit 3 is attached at a position on the outer surface of the flow cell 2 as shown in FIG. 1A is hereinafter described.

The light emitted from the light-casting unit 1 (measurement light) obliquely enters the flow cell 2 and passes through the sample liquid flowing through the passage in the flow cell 2. Since the refractive index $n_2$ of the material of the conduit of the flow cell 2 is higher than the refractive index $n_1$ of the air, the measurement light is totally reflected at the interface between the conduit of the flow cell 2 and the air (i.e. at the outer surface of the flow cell 2) and once more passes through the sample liquid. In the configuration of FIG. 1A, the detecting unit 3 is attached on the side opposite from the aforementioned interface, near the position at which the measurement light that has passed through the sample liquid after undergoing the total reflection one time reaches the interface between the conduit of the flow cell 2 and the air. As noted earlier, the refractive index $n_4$ of the connecting element 32 in contact with the outer surface of the flow cell 2 is equal to or higher than the refractive index $n_2$ of the material of the conduit of the flow cell 2. Therefore, no total reflection occurs at this interface and the measurement light passes through the interface, penetrating through the connecting element 32 to the photodetector element 31. That is to say, the connecting element 32 has the function of efficiently inducing a leakage of light from the flow cell 2.

The measurement light undergoes absorption by the components in the sample liquid mainly during its passage through the sample liquid. In the configuration of FIG. 1A, the measurement light reaches the photodetector element 31 after travelling a distance of 2×P which is approximately two times the length P of the optical path which obliquely passes through the sample liquid. Accordingly, the photodetector element 31 produces a signal corresponding to the amount of measurement light which has undergone absorption on this path having a length of 2×P.

When the attachment position of the detecting unit 3 is changed as shown in FIG. 1B by the measurer, the measurement operation will be as follows. It should be noted that the dotted line in FIG. 1B indicates the position of the detecting unit 3 in FIG. 1A.

The measurement light emitted from the light-casting unit 1 obliquely enters the flow cell 2, passes through the sample liquid and undergoes total reflection at the interface between the conduit of the flow cell 2 and the air, as in the case of FIG. 1A. Since the detecting unit 3 in the present case is located at a farther position from the light-casting unit 1, the measurement light which has passed through the sample liquid for the second time is once more totally reflected at the interface between the conduit of the flow cell 2 and the air. After repeatedly undergoing the total reflection multiple times, the measurement light reaches the position where the detecting unit 3 is attached. At this position, no total reflection occurs at the interface and the measurement light passes through it, penetrating through the connecting element 32 to the photodetector element 31. In the configuration of FIG. 1B, the measurement light reaches the photodetector element 31 after travelling a distance of 6×P which is approximately six times the length P of the optical path which obliquely passes through the sample liquid. Accordingly the photodetector element 31 produces a signal corresponding to the amount of measurement light which has undergone absorption on this path having a length of 6×P.

In the example of FIGS. 1A and 1B, only the measurement light which travels along the beam axis of the light emitted from the light-casting unit 1 is taken into account. Actually, as noted earlier, the light emitted from the light-casting unit 1 spreads within a predetermined solid angle. Therefore, as shown in FIG. 2, not only the ray of light which has undergone total reflection a specific number of times but also other rays of measurement light which have undergone total reflection different numbers of times may possibly reach the detecting unit 3 attached at a certain a position on the outer surface of the flow cell 2. However, whichever path the light follows while undergoing total reflection, the optical path length to the detecting unit 3 generally becomes shorter as the detecting unit 3 comes closer to the light-casting unit 1 within a predetermined range along the central axis of the flow cell 2. In other words, the average optical path length of the measurement light reaching the detecting unit 3 after the repetition of the total reflection can be regulated by changing (moving) the attachment position of the detecting unit 3 along the central axis of the flow cell 2. Therefore, for example, when the sample liquid has a low concentration and the absorbance per unit length of the optical path is accordingly low, the measurer can improve the detection sensitivity by attaching the detecting unit 3 at a distant position from the light-casting unit 1 so as to increase the average optical path length.

Figure 3A:
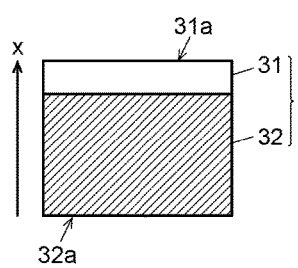
FIGS. 3A-3C are diagrams showing a configuration example of the detecting unit.
Figure 3B:
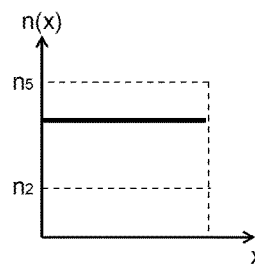
Figure 3C:
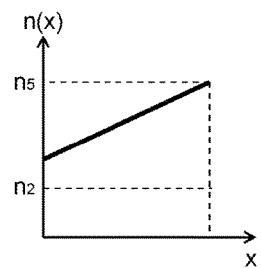

As noted earlier, the material of the connecting element 32 in the detecting unit 3 satisfies the condition that its refractive index $n_4$ be equal to or higher than the refractive index $n_2$ of the material of the flow cell 2 as well as equal to or lower than refractive index $n_5$ of the material of the light-receiving surface of the photodetector element 31. The refractive index $n_4$ may be uniform (see FIG. 3B. However, in order to maximally suppress the loss of light at the interface between the flow cell 2 and the connecting element 32 and thereby more efficiently extract light from the flow cell 2, the refractive index $n_4$ may preferably be made to gradually increase in the direction from the contact surface 32a facing the flow cell 2 to the contact surface 31a facing the photodetector element 31, as shown in FIG. 3C ; e.g. $n_4$ may gently increase from $n_2$ to $n_5$. Such a gradient of refractive index can be easily realized, for example, by giving the connecting element 32 a multilayer film structure. A moth-eye structure commonly used for antireflection films or the like may also be adopted to gradually change the refractive index. Although the change of the refractive index in FIG. 3C is linear, the change may alternatively be a curved or step-like change.

In the absorption measurement device in the previous embodiment, the measurement light from the light-casting unit 1 is obliquely cast into the flow cell 2. One advantage of such a configuration is that it allows the passage for introducing the sample liquid into the flow cell 2 or extracting the sample liquid from the flow cell 2 to be connected straight to the flow cell 2. Such a straight connection of the passage reduces the diffusion of light at the connected area and improves the light use efficiency.

Figure 4:
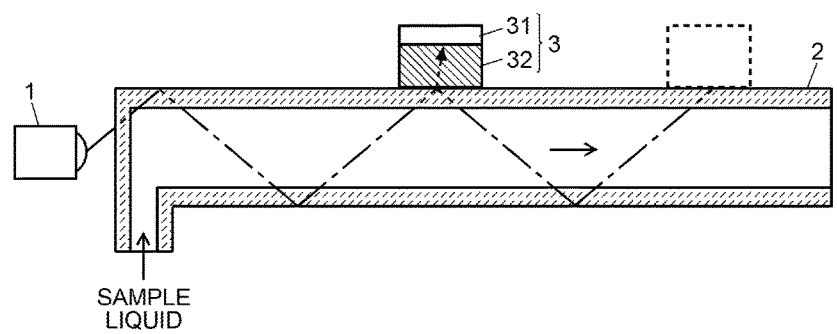
FIG. 4 is a schematic configuration diagram of an absorbance measurement device as another embodiment of the present invention.

Needless to say, as shown by one example in FIG. 4, the light from the light-casting unit 1 may be made to enter the flow cell 2 in a direction parallel to the central axis of the flow cell 2. That is to say, the measurement light may be incident from any direction as long as the measurement light can be introduced into the flow cell 2 so that the measurement light is totally reflected as the outer surface of the conduit of the flow cell 2.

In the examples of FIGS. 1A and 1B as well as FIG. 4, the flow cell 2 is shaped like a straight tube. However, the flow cell 2 does not need to have a straight tubular shape but may have a curved shape, flexed shape or the like.

Figure 5:
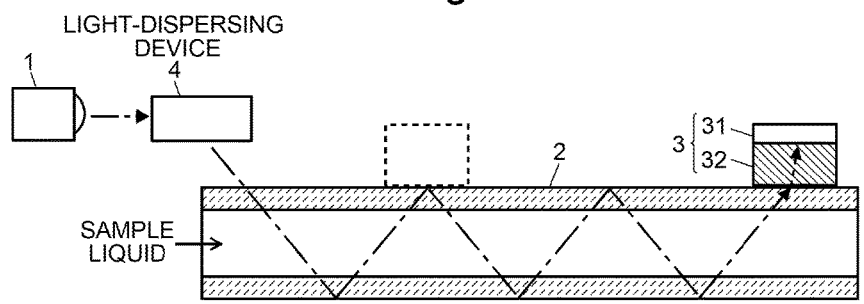
FIG. 5 is a schematic configuration diagram of an absorbance measurement device as another embodiment of the present invention.

In the previous embodiments, an LED which emits light within a narrow wavelength range is used as the light source. FIG. 5 shows another possible example, in which a deuterium lamp or another type of light source having a wide range of emission wavelength is used in the light-casting unit 1. The emitted light is introduced into a light-dispersing device 4 to extract monochromatic light having a specific wavelength. This monochromatic light is cast into the flow cell 2.

FIG. 6 shows still another possible example, in which the light emitted from the light-casting unit 1 using a light source having a wide range of emission wavelength is directly (i.e. without being changed into monochromatic light) cast into the flow cell 2. After undergoing absorption in the sample liquid, the measurement light is extracted from the flow cell 2 and subsequently introduced into the light-dispersing device 4 to extract monochromatic light having a specific wavelength. This monochromatic light is cast into the flow cell 2. In the present case, a photodiode array may be used as the photodetector element 31, and the light dispersed into wavelengths by the light-dispersing device 4 may be simultaneously detected with the photosensitive elements of the photodiode array. By this system, not only the absorbance at a specific wavelength but also an absorption spectrum can be measured. Furthermore, as shown by one example in FIG. 7, two light-dispersing devices 4A and 4B may be provided on both the light-casting side and the light-detecting side.

In the previous embodiments, the detecting unit 3 is provided only at one location in the circumferential direction of the outer surface of the flow cell 2. It is also possible to provide the detecting unit 3 over the entire circumference of the outer surface of the flow cell 2, as shown by one example in FIG. 8, in which the detecting unit 3 has an annular shape surrounding the flow cell 2. This configuration allows light to be efficiently extracted from the flow cell 2 and detected.

The optical measurement device according to the present invention is available not only for absorption measurement but also for fluorescence measurement or Raman-scattered light measurement, because detection signals in fluorescence measurement or Raman-scattered light measurement are also dependent on the optical path length. It should be noted that the wavelength of the light to be detected in the fluorescence measurement or Raman-scattered light measurement is different from that of the light cast into the sample liquid (the measurement light in the previous examples); the cast light will eventually be unnecessary light or a kind of noise light. Therefore, for the fluorescence measurement or Raman-scattered light measurement, the configuration as shown in FIG. 6 or 7 having the light-dispersing device 4 or 4B placed on the detecting side may preferably be adopted to selectively extract light having the target wavelength or measure a spectrum within a predetermined wavelength range. Additionally, since fluorescence and Raman-scattered light are emitted in all directions, the configuration as shown in FIG. 8 is particularly useful for efficiently collecting the light to be detected.

In the previous embodiments, only one detecting unit 3 is provided on the flow cell 2. It is also possible to provide a plurality of detecting units 3 on the single flow cell 2 and simultaneously detect light with those detecting units 3. This allows a measurement to be performed with different sensitivities corresponding to a plurality of different optical path lengths.

Any of the previous embodiments is a mere example of the present invention, and any further change, modification or addition appropriately made within the spirit of the present invention will evidently fall within the scope of claims of the present application. For example, although the sample cells in the previous embodiments are flow cells, the present invention is also applicable in a device using a sample cell which holds a sample liquid, i.e. in which the sample liquid is stored and does not flow through.

REFERENCE SIGNS LIST

1 . . . Light-Casting Unit
2 . . . Flow Cell
3 . . . Detecting Unit
31 . . . Photodetector Element
31a, 32a . . . Contact Surface
32 . . . Connecting Element
4, 4A, 4B . . . Light-Dispersing Device

The invention claimed is:

1. An optical measurement device, comprising:
a) an optically transparent sample cell which is a tubular container through which a sample liquid is to be passed or in which a sample liquid is to be contained;
b) a measurement-light casting unit for casting measurement light into the sample cell along an axis of the sample cell or in a direction oblique to the axis of the sample cell; and
c) a detecting unit for detecting light coming from the sample cell when the measurement light is cast from the measurement-light casting unit into the sample cell, the light being either the measurement light transmitted through the sample cell or light emitted from the sample liquid in response to the measurement light, and the detecting unit including: a photodetector element for performing photoelectric conversion; and a connecting element placed between the sample cell and the photodetector element in such a manner as to have a portion being in contact with an outer surface of the sample cell and another portion being in contact with the photodetector element, the connecting element being made of a material which allows transmission of light and whose refractive index is equal to or higher than a refractive index of a material of a wall of the sample cell,
where a contact position of the detecting unit on the sample cell is changeable.

2. The optical measurement device according to claim 1, wherein the detecting unit is provided over an entire circumference of the outer surface of the sample cell.

3. The optical measurement device according to claim 1, wherein the connecting element has the refractive index increasing from the surface which is in contact with the sample cell toward the surface which is in contact with the photodetector element.

4. The optical measurement device according to claim 1, wherein the connecting element is made of the material whose refractive index is equal to or higher than the refractive index of the material of the wall of the sample cell as well as equal to or lower than the refractive index of the material of the light-receiving surface of the photodetector element.

5. The optical measurement device according to claim 1, wherein the connecting element is made of a refractive index dispersion polymer, a gel-like member or silicone.

6. The optical measurement device according to claim 1, wherein the contact position of the detecting unit on the sample cell is changeable in such a manner that the contact position of the detecting unit on the sample cell is set at a position closer to the measurement-light casting unit so as to shorten an average optical path length when the sample liquid has a high concentration, while the contact position of the detecting unit on the sample cell is set at a position farther from the measurement-light casting unit so as to elongate average optical path length when the sample liquid has a low concentration.

7. An optical measurement device, comprising:
a) an optically transparent sample cell which is a tubular container through which a sample liquid is to be passed or in which a sample liquid is to be contained;
b) a measurement-light casting unit for casting measurement light into the sample cell along an axis of the sample cell or in a direction oblique to the axis of the sample cell; and
c) a detecting unit for detecting light coming from the sample cell when the measurement light is cast from the measurement-light casting unit into the sample cell, the light being either the measurement light transmitted through the sample cell or light emitted from the sample liquid in response to the measurement light, and the detecting unit including: a photodetector element for performing photoelectric conversion; a light-dispersing element for extracting a specific wavelength of light and for introducing the extracted light into the photodetector element; and a connecting element placed between the sample cell and the light-dispersing element in such a manner that a portion of the connecting element is in contact with an outer surface of the sample cell and another portion is in contact with the light-dispersing element, the connecting element being made of a material which allows transmission of light and whose refractive index is equal to or higher than a refractive index of a material of a wall of the sample cell, where a contact position of the detecting unit on the sample cell is changeable.

* * * * *